(12) United States Patent
Gorochow et al.

(10) Patent No.: US 11,457,926 B2
(45) Date of Patent: Oct. 4, 2022

(54) IMPLANT HAVING AN INTRASACCULAR SECTION AND INTRAVASCULAR SECTION

(71) Applicant: DePuy Synthes Products, Inc., Raynham, MA (US)

(72) Inventors: Lacey Gorochow, Raynham, MA (US); Ruijiao Xu, Raynham, MA (US); Yusuf Sevencan, Raynham, MA (US)

(73) Assignee: DePuy Synthes Products, Inc., Raynham, MA (US)

(*) Notice: Subject to any disclaimer, the term of this patent is extended or adjusted under 35 U.S.C. 154(b) by 195 days.

(21) Appl. No.: 16/718,912

(22) Filed: Dec. 18, 2019

(65) Prior Publication Data

US 2021/0186518 A1    Jun. 24, 2021

(51) Int. Cl.
*A61B 17/12*    (2006.01)
*A61M 25/00*    (2006.01)
(Continued)

(52) U.S. Cl.
CPC .. *A61B 17/12172* (2013.01); *A61B 17/12113* (2013.01); *A61B 2017/00867* (2013.01);
(Continued)

(58) Field of Classification Search
CPC ........ A61B 17/12172; A61B 17/12113; A61B 17/12122; A61B 17/1207; A61B 17/12031; A61B 17/12036; A61B 17/12022
See application file for complete search history.

(56) References Cited

U.S. PATENT DOCUMENTS 2,849,002 A    8/1958   Oddo
3,480,017 A    11/1969  Shute
(Continued)

FOREIGN PATENT DOCUMENTS

CA    2395796 A1    7/2001
CA    2 431 594 A1  9/2002
(Continued)

OTHER PUBLICATIONS

Schaffer, Advanced Materials & Processes, Oct. 2002, pp. 51-54.
(Continued)

*Primary Examiner* — Katherine M Shi
*Assistant Examiner* — Mohammed S Adam
(74) *Attorney, Agent, or Firm* — Troutman Pepper Hamilton Sanders LLP

(57) ABSTRACT

An example implant can have a tubular braid. The tubular braid can have an intrasaccular section, an intravascular section, a pinched section, and a predetermined shape. In the predetermined shape, the intrasaccular section can have a sack and an opening. The pinched section can be positioned approximate the opening. The intravascular section can be substantially disk shaped and positioned to occlude the opening. The tubular braid can be movable from a collapsed shape sized to traverse a catheter to an implanted shape based at least in part on the predetermined shape. In the implanted shape, the intrasaccular section of the braid can be sized to be positioned within an aneurysm's sac and the intravascular section of the braid can be sized to appose a blood vessel wall approximate an aneurysm's neck.

18 Claims, 10 Drawing Sheets

(51) Int. Cl.
*A61B 90/00* (2016.01)
*A61B 17/00* (2006.01)

(52) U.S. Cl.
CPC .............. *A61B 2090/3966* (2016.02); *A61M 2025/0042* (2013.01)

(56) References Cited

U.S. PATENT DOCUMENTS

| | | |
|---|---|---|
| 4,085,757 A | 4/1978 | Pevsner |
| 4,282,875 A | 4/1981 | Serbinenko et al. |
| 4,364,392 A | 12/1982 | Strother et al. |
| 4,395,806 A | 8/1983 | Wonder et al. |
| 4,517,979 A | 5/1985 | Pecenka |
| 4,545,367 A | 10/1985 | Tucci |
| 4,836,204 A | 6/1989 | Landymore et al. |
| 4,991,602 A | 2/1991 | Amplatz et al. |
| 5,002,556 A | 3/1991 | Ishida et al. |
| 5,025,060 A | 6/1991 | Yabuta et al. |
| 5,065,772 A | 11/1991 | Cox, Jr. |
| 5,067,489 A | 11/1991 | Lind |
| 5,122,136 A | 6/1992 | Guglielmi et al. |
| 5,192,301 A | 3/1993 | Kamiya et al. |
| 5,261,916 A | 11/1993 | Engelson |
| 5,304,195 A | 4/1994 | Twyford, Jr. et al. |
| 5,334,210 A | 8/1994 | Gianturco |
| 5,350,397 A | 9/1994 | Palermo |
| 5,423,829 A | 6/1995 | Pham et al. |
| 5,624,449 A | 4/1997 | Pham et al. |
| 5,645,558 A | 7/1997 | Horton |
| 5,733,294 A | 3/1998 | Forber et al. |
| 5,891,128 A | 4/1999 | Gia et al. |
| 5,916,235 A | 6/1999 | Guglielmi |
| 5,928,260 A | 7/1999 | Chin et al. |
| 5,935,148 A | 8/1999 | Villar |
| 5,941,249 A | 8/1999 | Maynard |
| 5,951,599 A | 9/1999 | McCrory |
| 5,964,797 A | 10/1999 | Ho |
| 6,007,573 A | 12/1999 | Wallace et al. |
| 6,024,756 A | 2/2000 | Pham |
| 6,036,720 A | 3/2000 | Abrams |
| 6,063,070 A | 5/2000 | Eder |
| 6,063,100 A | 5/2000 | Diaz et al. |
| 6,063,104 A | 5/2000 | Villar |
| 6,080,191 A | 6/2000 | Thaler |
| 6,086,577 A | 7/2000 | Ken et al. |
| 6,096,021 A | 8/2000 | Helm et al. |
| 6,113,609 A | 9/2000 | Adams |
| 6,123,714 A | 9/2000 | Gia et al. |
| 6,168,615 B1 | 1/2001 | Ken |
| 6,168,622 B1 | 1/2001 | Mazzocchi |
| 6,193,708 B1 | 2/2001 | Ken et al. |
| 6,221,086 B1 | 4/2001 | Forber |
| 6,270,515 B1 | 8/2001 | Linden et al. |
| 6,315,787 B1 | 11/2001 | Tsugita et al. |
| 6,331,184 B1 | 12/2001 | Abrams |
| 6,334,048 B1 | 12/2001 | Edvardsson et al. |
| 6,346,117 B1 | 2/2002 | Greenhalgh |
| 6,350,270 B1 | 2/2002 | Roue |
| 6,375,606 B1 | 4/2002 | Garbaldi et al. |
| 6,375,668 B1 | 4/2002 | Gifford |
| 6,379,329 B1 | 4/2002 | Naglreiter et al. |
| 6,391,037 B1 | 5/2002 | Greenhalgh |
| 6,419,686 B1 | 7/2002 | McLeod et al. |
| 6,428,558 B1 | 8/2002 | Jones |
| 6,454,780 B1 | 9/2002 | Wallace |
| 6,463,317 B1 | 10/2002 | Kucharczyk et al. |
| 6,506,204 B2 | 1/2003 | Mazzocchi et al. |
| 6,527,919 B1 | 3/2003 | Roth |
| 6,547,804 B2 | 4/2003 | Porter et al. |
| 6,551,303 B1 | 4/2003 | Van Tassel et al. |
| 6,569,179 B2 | 5/2003 | Teoh |
| 6,569,190 B2 | 5/2003 | Whalen, II et al. |
| 6,572,628 B2 | 6/2003 | Dominguez |
| 6,589,230 B2 | 7/2003 | Gia et al. |
| 6,589,256 B2 | 7/2003 | Forber |
| 6,605,102 B1 | 8/2003 | Mazzocchi et al. |
| 6,620,152 B2 | 9/2003 | Guglielmi |
| 6,669,719 B2 | 12/2003 | Wallace et al. |
| 6,689,159 B2 | 2/2004 | Lau et al. |
| 6,746,468 B1 | 6/2004 | Sepetka |
| 6,780,196 B2 | 8/2004 | Chin et al. |
| 6,802,851 B2 | 10/2004 | Jones |
| 6,811,560 B2 | 11/2004 | Jones |
| 6,833,003 B2 | 12/2004 | Jones et al. |
| 6,846,316 B2 | 1/2005 | Abrams |
| 6,849,081 B2 | 2/2005 | Sepetka et al. |
| 6,855,154 B2 | 2/2005 | Abdel-Gawwad |
| 6,949,116 B2 | 9/2005 | Solymar et al. |
| 6,964,657 B2 | 11/2005 | Cragg et al. |
| 6,964,671 B2 | 11/2005 | Cheng |
| 6,994,711 B2 | 2/2006 | Hieshima et al. |
| 7,044,134 B2 | 5/2006 | Khairkhahan et al. |
| 7,083,632 B2 | 8/2006 | Avellanet |
| 7,093,527 B2 | 8/2006 | Rapaport et al. |
| 7,128,736 B1 | 10/2006 | Abrams et al. |
| 7,152,605 B2 | 12/2006 | Khairkhahan et al. |
| 7,153,323 B1 | 12/2006 | Teoh |
| 7,195,636 B2 | 3/2007 | Avellanet et al. |
| 7,229,454 B2 | 6/2007 | Tran et al. |
| 7,229,461 B2 | 6/2007 | Chin et al. |
| 7,309,345 B2 | 12/2007 | Wallace |
| 7,371,249 B2 | 5/2008 | Douk et al. |
| 7,377,932 B2 | 5/2008 | Mitelberg et al. |
| 7,410,482 B2 | 8/2008 | Murphy et al. |
| 7,572,288 B2 | 8/2009 | Cox |
| 7,597,704 B2 | 10/2009 | Frazier et al. |
| 7,608,088 B2 | 10/2009 | Jones |
| 7,695,488 B2 | 4/2010 | Berenstein et al. |
| 7,713,264 B2 | 5/2010 | Murphy |
| 7,744,652 B2 | 6/2010 | Morsi |
| 7,892,248 B2 | 2/2011 | Tran |
| 7,985,238 B2 | 7/2011 | Balgobin et al. |
| RE42,758 E | 9/2011 | Ken |
| 8,016,852 B2 | 9/2011 | Ho |
| 8,021,416 B2 | 9/2011 | Abrams |
| 8,025,668 B2 | 9/2011 | McCartney |
| 8,034,061 B2 | 10/2011 | Amplatz et al. |
| 8,048,145 B2 | 11/2011 | Evans et al. |
| 8,062,325 B2 | 11/2011 | Mitelberg et al. |
| 8,075,585 B2 | 12/2011 | Lee et al. |
| 8,142,456 B2 | 3/2012 | Rosqueta et al. |
| 8,221,483 B2 | 7/2012 | Ford et al. |
| 8,261,648 B1 | 9/2012 | Marchand et al. |
| 8,267,923 B2 | 9/2012 | Murphy |
| 8,361,106 B2 | 1/2013 | Solar et al. |
| 8,361,138 B2 | 1/2013 | Adams |
| 8,372,114 B2 | 2/2013 | Hines |
| 8,398,671 B2 | 3/2013 | Chen |
| 8,430,012 B1 | 4/2013 | Marchand |
| 8,454,633 B2 | 6/2013 | Amplatz et al. |
| 8,523,897 B2 | 9/2013 | van der Burg et al. |
| 8,523,902 B2 | 9/2013 | Heaven et al. |
| 8,551,132 B2 | 10/2013 | Eskridge et al. |
| 8,777,974 B2 | 7/2014 | Amplatz et al. |
| 8,900,304 B1 | 12/2014 | Alobaid |
| 8,974,512 B2 | 3/2015 | Aboytes et al. |
| 8,992,568 B2 | 3/2015 | Duggal et al. |
| 8,998,947 B2 | 4/2015 | Aboytes et al. |
| 9,055,948 B2 | 6/2015 | Jaeger et al. |
| 9,107,670 B2 | 8/2015 | Hannes et al. |
| 9,161,758 B2 | 10/2015 | Figulla et al. |
| 9,232,992 B2 | 1/2016 | Heidner |
| 9,259,337 B2 | 2/2016 | Cox et al. |
| 9,314,326 B2 | 4/2016 | Wallace et al. |
| 9,351,715 B2 | 5/2016 | Mach |
| 9,414,842 B2 | 8/2016 | Glimsdale et al. |
| 9,526,813 B2 | 12/2016 | Cohn et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |

(56) References Cited

U.S. PATENT DOCUMENTS

| | | |
|---|---|---|
| 9,549,830 B2 | 1/2017 | Bruszewski et al. |
| 9,554,805 B2 | 1/2017 | Tompkins et al. |
| 9,561,096 B2 | 2/2017 | Kim et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,585,669 B2 | 3/2017 | Becking et al. |
| 9,615,832 B2 | 4/2017 | Bose et al. |
| 9,615,951 B2 | 4/2017 | Bennett et al. |
| 9,622,753 B2 | 4/2017 | Cox |
| 9,629,635 B2 | 4/2017 | Hewitt et al. |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,681,861 B2 | 6/2017 | Heisel et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,918,720 B2 | 3/2018 | Marchand et al. |
| 9,955,976 B2 | 5/2018 | Hewitt et al. |
| 10,004,510 B2 | 6/2018 | Gerberding |
| 10,130,372 B2 | 11/2018 | Griffin |
| 10,307,148 B2 | 6/2019 | Heisel et al. |
| 10,327,781 B2 | 6/2019 | Divino et al. |
| 10,342,546 B2 | 7/2019 | Sepetka et al. |
| 10,517,604 B2 | 12/2019 | Bowman et al. |
| 10,653,425 B1 | 5/2020 | Gorochow et al. |
| 10,716,573 B2 | 7/2020 | Connor |
| 2002/0068974 A1 | 6/2002 | Kuslich et al. |
| 2002/0082638 A1 | 6/2002 | Porter et al. |
| 2002/0143349 A1 | 10/2002 | Gifford, III et al. |
| 2002/0147497 A1 | 10/2002 | Belef et al. |
| 2002/0188314 A1 | 12/2002 | Anderson et al. |
| 2003/0028209 A1 | 2/2003 | Teoh et al. |
| 2003/0120337 A1 | 6/2003 | Van Tassel et al. |
| 2003/0171739 A1 | 9/2003 | Murphy et al. |
| 2003/0176884 A1 | 9/2003 | Berrada et al. |
| 2003/0181927 A1 | 9/2003 | Wallace |
| 2003/0181945 A1 | 9/2003 | Opolski |
| 2003/0195553 A1 | 10/2003 | Wallace |
| 2003/0216772 A1 | 11/2003 | Konya |
| 2004/0034366 A1 | 2/2004 | van der Burg et al. |
| 2004/0034386 A1 | 2/2004 | Fulton et al. |
| 2004/0044391 A1 | 3/2004 | Porter |
| 2004/0087998 A1 | 5/2004 | Lee et al. |
| 2004/0098027 A1 | 5/2004 | Teoh et al. |
| 2004/0127935 A1 | 7/2004 | Van Tassel et al. |
| 2004/0133222 A1 | 7/2004 | Tran et al. |
| 2004/0153120 A1 | 8/2004 | Seifert et al. |
| 2004/0210297 A1 | 10/2004 | Lin et al. |
| 2004/0254594 A1 | 12/2004 | Alfaro |
| 2005/0021016 A1 | 1/2005 | Malecki et al. |
| 2005/0021072 A1 | 1/2005 | Wallace |
| 2005/0159771 A1 | 7/2005 | Petersen |
| 2005/0177103 A1 | 8/2005 | Hunter et al. |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1 | 3/2006 | Guterman |
| 2006/0106421 A1 | 5/2006 | Teoh |
| 2006/0155323 A1 | 7/2006 | Porter et al. |
| 2006/0155367 A1 | 7/2006 | Hines |
| 2006/0167494 A1 | 7/2006 | Suddaby |
| 2006/0247572 A1 | 11/2006 | McCartney |
| 2007/0088387 A1 | 4/2007 | Eskridge et al. |
| 2007/0106311 A1 | 5/2007 | Wallace et al. |
| 2007/0208376 A1 | 6/2007 | Meng |
| 2007/0162071 A1 | 7/2007 | Burkett et al. |
| 2007/0167876 A1 | 7/2007 | Euteneuer et al. |
| 2007/0173928 A1 | 7/2007 | Morsi |
| 2007/0186933 A1 | 8/2007 | Domingo |
| 2007/0191884 A1 | 8/2007 | Eskridge et al. |
| 2007/0233188 A1 | 10/2007 | Hunt et al. |
| 2007/0265656 A1 | 11/2007 | Amplatz et al. |
| 2007/0288083 A1 | 12/2007 | Hines |
| 2008/0097495 A1 | 4/2008 | Feller, III et al. |
| 2008/0103505 A1 | 5/2008 | Fransen |
| 2008/0119886 A1 | 5/2008 | Greenhalgh et al. |
| 2008/0281350 A1 | 11/2008 | Sepetka |
| 2009/0036877 A1 | 2/2009 | Nardone et al. |
| 2009/0062841 A1 | 3/2009 | Amplatz et al. |
| 2009/0099647 A1 | 4/2009 | Glimsdale et al. |
| 2009/0227983 A1 | 9/2009 | Griffin et al. |
| 2009/0281557 A1 | 11/2009 | Sander et al. |
| 2009/0287291 A1 | 11/2009 | Becking et al. |
| 2009/0287297 A1 | 11/2009 | Cox |
| 2009/0318941 A1 | 12/2009 | Sepetka |
| 2010/0023046 A1 | 1/2010 | Heidner et al. |
| 2010/0023048 A1 | 1/2010 | Mach |
| 2010/0063573 A1 | 3/2010 | Hijlkema |
| 2010/0063582 A1 | 3/2010 | Rudakov |
| 2010/0069948 A1 | 3/2010 | Veznedaroglu et al. |
| 2010/0168781 A1 | 7/2010 | Berenstein |
| 2010/0211156 A1 | 8/2010 | Linder et al. |
| 2010/0324649 A1 | 12/2010 | Mattsson |
| 2011/0046658 A1 | 2/2011 | Conner et al. |
| 2011/0054519 A1 | 3/2011 | Neuss |
| 2011/0112588 A1 | 5/2011 | Linderman et al. |
| 2011/0137317 A1 | 6/2011 | O'Halloran et al. |
| 2011/0152993 A1 | 6/2011 | Marchand et al. |
| 2011/0196413 A1 | 8/2011 | Wallace |
| 2011/0319978 A1 | 12/2011 | Schaffer |
| 2012/0010644 A1 | 1/2012 | Sideris et al. |
| 2012/0071911 A1 | 3/2012 | Sadasivan |
| 2012/0165732 A1 | 6/2012 | Müller |
| 2012/0191123 A1 | 7/2012 | Brister et al. |
| 2012/0283768 A1 | 11/2012 | Cox et al. |
| 2012/0310270 A1 | 12/2012 | Murphy |
| 2012/0323267 A1 | 12/2012 | Ren |
| 2012/0330341 A1 | 12/2012 | Becking et al. |
| 2013/0035665 A1 | 2/2013 | Chu et al. |
| 2013/0035712 A1 | 2/2013 | Theobald et al. |
| 2013/0066357 A1 | 3/2013 | Aboytes et al. |
| 2013/0079864 A1 | 3/2013 | Boden |
| 2013/0110066 A1 | 5/2013 | Sharma et al. |
| 2013/0204351 A1 | 8/2013 | Cox et al. |
| 2013/0211495 A1 | 8/2013 | Halden et al. |
| 2013/0261658 A1 | 10/2013 | Lorenzo et al. |
| 2013/0261730 A1 | 10/2013 | Bose et al. |
| 2013/0274863 A1 | 10/2013 | Cox et al. |
| 2013/0345738 A1 | 12/2013 | Eskridge |

(56) References Cited

U.S. PATENT DOCUMENTS

| | | |
|---|---|---|
| 2014/0005714 A1 | 1/2014 | Quick et al. |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0135812 A1 | 5/2014 | Divino et al. |
| 2014/0200607 A1 | 7/2014 | Sepetka et al. |
| 2014/0257360 A1 | 9/2014 | Keillor |
| 2014/0257361 A1 | 9/2014 | Prom |
| 2014/0277013 A1 | 9/2014 | Sepetka et al. |
| 2014/0358178 A1 | 12/2014 | Hewitt et al. |
| 2015/0057703 A1 | 2/2015 | Ryan et al. |
| 2015/0209050 A1 | 7/2015 | Aboytes et al. |
| 2015/0272589 A1 | 10/2015 | Lorenzo |
| 2015/0313605 A1 | 11/2015 | Griffin |
| 2015/0342613 A1 | 12/2015 | Aboytes et al. |
| 2015/0374483 A1 | 12/2015 | Janardhan et al. |
| 2016/0022445 A1 | 1/2016 | Ruvalcaba et al. |
| 2016/0030050 A1 | 2/2016 | Franano et al. |
| 2016/0192912 A1 | 7/2016 | Kassab et al. |
| 2016/0249934 A1 | 9/2016 | Hewitt et al. |
| 2016/0249935 A1* | 9/2016 | Hewitt ............... A61B 17/1214 606/200 |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079661 A1 | 3/2017 | Bardsley et al. |
| 2017/0079662 A1 | 3/2017 | Rhee et al. |
| 2017/0079671 A1 | 3/2017 | Morero et al. |
| 2017/0079680 A1 | 3/2017 | Bowman |
| 2017/0079717 A1 | 3/2017 | Walsh et al. |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0114350 A1 | 8/2017 | Shimizu et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340333 A1 | 11/2017 | Badruddin et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0140305 A1 | 5/2018 | Connor |
| 2018/0206850 A1 | 7/2018 | Wang et al. |
| 2018/0242979 A1 | 8/2018 | Lorenzo |
| 2018/0303531 A1 | 10/2018 | Sanders et al. |
| 2018/0338767 A1 | 11/2018 | Dasnurkar et al. |
| 2019/0008522 A1 | 1/2019 | Lorenzo |
| 2019/0223878 A1 | 1/2019 | Lorenzo et al. |
| 2019/0110796 A1 | 4/2019 | Jayaraman |
| 2019/0142567 A1 | 5/2019 | Janardhan et al. |
| 2019/0192162 A1 | 6/2019 | Lorenzo |
| 2019/0192167 A1 | 6/2019 | Lorenzo |
| 2019/0192168 A1 | 6/2019 | Lorenzo |
| 2019/0223879 A1 | 7/2019 | Jayaraman |
| 2019/0223881 A1 | 9/2019 | Hewitt et al. |
| 2019/0328398 A1 | 10/2019 | Lorenzo |
| 2019/0357914 A1 | 11/2019 | Gorochow et al. |
| 2019/0365385 A1 | 12/2019 | Gorochow et al. |
| 2020/0000477 A1 | 1/2020 | Nita et al. |
| 2020/0069313 A1 | 3/2020 | Xu et al. |
| 2020/0268365 A1 | 8/2020 | Hebert et al. |

FOREIGN PATENT DOCUMENTS

| | | |
|---|---|---|
| CA | 2598048 A1 | 5/2008 |
| CN | 204 683 687 U | 10/2015 |
| DE | 102008015781 A1 | 10/2009 |
| DE | 102010053111 A1 | 6/2012 |
| DE | 102009058132 B4 | 7/2014 |
| DE | 10 2013 106031 A1 | 12/2014 |
| DE | 202008018523 U1 | 4/2015 |
| DE | 102011102955 B4 | 5/2018 |
| EP | 902704 B1 | 3/1999 |
| EP | 1054635 B1 | 11/2000 |
| EP | 1295563 A1 | 3/2003 |
| EP | 1441649 B1 | 8/2004 |
| EP | 1483009 B1 | 12/2004 |
| EP | 1527753 B1 | 5/2005 |
| EP | 1569565 B1 | 9/2005 |
| EP | 1574169 B1 | 9/2005 |
| EP | 1494619 B1 | 1/2006 |
| EP | 1633275 B1 | 3/2006 |
| EP | 1659988 B1 | 5/2006 |
| EP | 1725185 B1 | 11/2006 |
| EP | 1862122 A1 | 12/2007 |
| EP | 1923005 B1 | 5/2008 |
| EP | 2063791 B1 | 6/2009 |
| EP | 2134263 B1 | 12/2009 |
| EP | 2157937 B1 | 3/2010 |
| EP | 2266456 A1 | 12/2010 |
| EP | 2324775 B1 | 5/2011 |
| EP | 2367482 B1 | 9/2011 |
| EP | 2387951 B1 | 11/2011 |

(56) References Cited

FOREIGN PATENT DOCUMENTS

| | | |
|---|---|---|
| EP | 2460476 A2 | 6/2012 |
| EP | 2468349 A1 | 6/2012 |
| EP | 2543345 A1 | 1/2013 |
| EP | 2567663 A1 | 3/2013 |
| EP | 2617386 A1 | 7/2013 |
| EP | 2623039 A1 | 8/2013 |
| EP | 2647343 A2 | 10/2013 |
| EP | 2848211 A1 | 3/2015 |
| EP | 2854704 B1 | 4/2015 |
| EP | 2923674 B1 | 9/2015 |
| EP | 2926744 A1 | 10/2015 |
| EP | 3146916 A1 | 3/2017 |
| EP | 3501429 A1 | 6/2019 |
| EP | 3517055 A1 | 7/2019 |
| JP | H04-47415 U | 4/1992 |
| JP | H07-37200 U | 7/1995 |
| JP | 2006-509578 A | 3/2006 |
| JP | 2013-509972 A | 3/2013 |
| JP | 2013537069 A | 9/2013 |
| JP | 2014-522268 A | 9/2014 |
| JP | 2016-502925 A | 2/2015 |
| WO | WO 9641589 A1 | 12/1996 |
| WO | WO 9905977 A1 | 2/1999 |
| WO | WO 9908607 A1 | 2/1999 |
| WO | WO 9930640 A1 | 6/1999 |
| WO | 2003073961 A1 | 9/2003 |
| WO | WO 03/086240 A1 | 10/2003 |
| WO | WO 2005020822 A1 | 3/2005 |
| WO | WO 2005074814 A2 | 8/2005 |
| WO | 2005117718 A1 | 12/2005 |
| WO | WO 2006034149 A2 | 3/2006 |
| WO | WO 2006052322 A2 | 5/2006 |
| WO | 2007/076480 A2 | 7/2007 |
| WO | WO 2008150346 A1 | 12/2008 |
| WO | WO 2008151204 A1 | 12/2008 |
| WO | WO 2009048700 A1 | 4/2009 |
| WO | WO 2009105365 A1 | 8/2009 |
| WO | WO 2009132045 A2 | 10/2009 |
| WO | WO 2009135166 A2 | 11/2009 |
| WO | WO 2010030991 A1 | 3/2010 |
| WO | WO 2011057002 A2 | 5/2011 |
| WO | WO 2012032030 A1 | 3/2012 |
| WO | WO 2012099704 A2 | 7/2012 |
| WO | WO 2012099909 A2 | 7/2012 |
| WO | WO 2012113554 A1 | 8/2012 |
| WO | WO 2013016618 A2 | 1/2013 |
| WO | WO 2013025711 A1 | 2/2013 |
| WO | WO 2013109309 A1 | 7/2013 |
| WO | WO 2013159065 A1 | 10/2013 |
| WO | WO 2013162817 A1 | 10/2013 |
| WO | WO 2014029835 A1 | 2/2014 |
| WO | WO 2014078286 A1 | 5/2014 |
| WO | WO 2014110589 A1 | 7/2014 |
| WO | WO 2014137467 A1 | 9/2014 |
| WO | WO 2015073704 A1 | 5/2015 |
| WO | 2015160721 A1 | 10/2015 |
| WO | 2015171268 A1 | 11/2015 |
| WO | WO 2015166013 A1 | 11/2015 |
| WO | WO 2015184075 A1 | 12/2015 |
| WO | WO 2015187196 A1 | 12/2015 |
| WO | WO 2016044647 A2 | 3/2016 |
| WO | WO 2016107357 A1 | 7/2016 |
| WO | WO 2016137997 A1 | 9/2016 |
| WO | 2017/161283 A1 | 9/2017 |
| WO | WO 2018051187 A1 | 3/2018 |
| WO | WO 2019/038293 A1 | 2/2019 |
| WO | WO 2012/034135 A1 | 3/2021 |

OTHER PUBLICATIONS

Partial European Search Report issued in corresponding European Patent Application No. 20 21 5196 dated Apr. 19, 2021 pp. 1-16.
Extended European Search Report issued in corresponding European Patent Application No. 19 21 5277 dated May 12, 2020 pp. 1-11.
Extended European Search Report dated May 2, 2019 in corresponding European Application No. 18214052.5 pp. 1-11.

\* cited by examiner

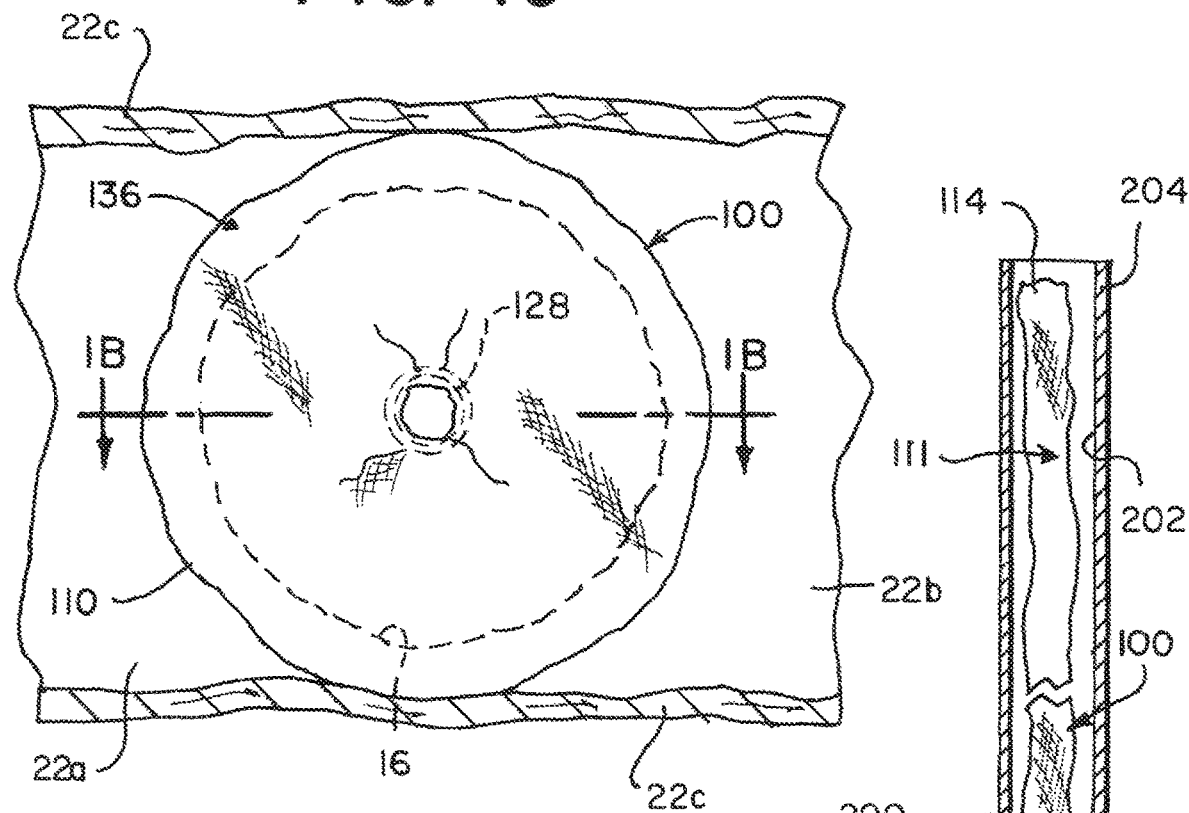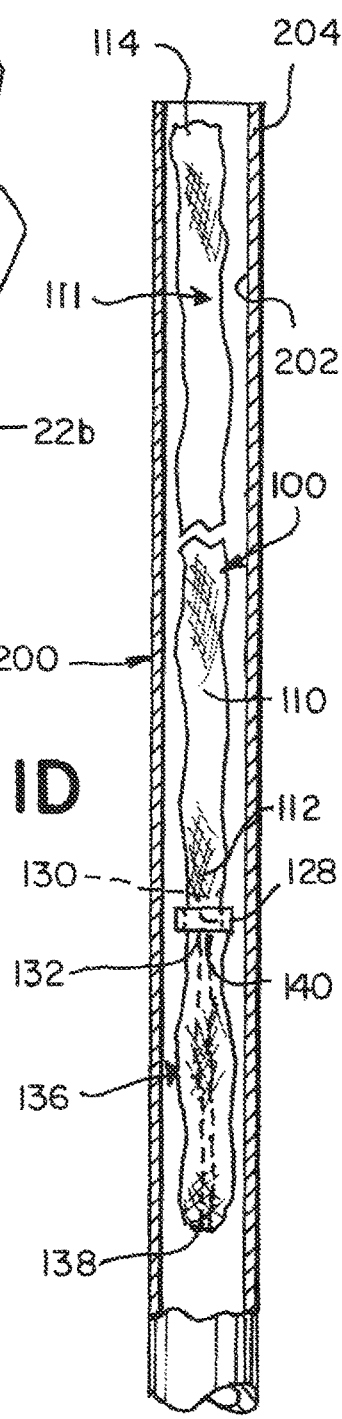

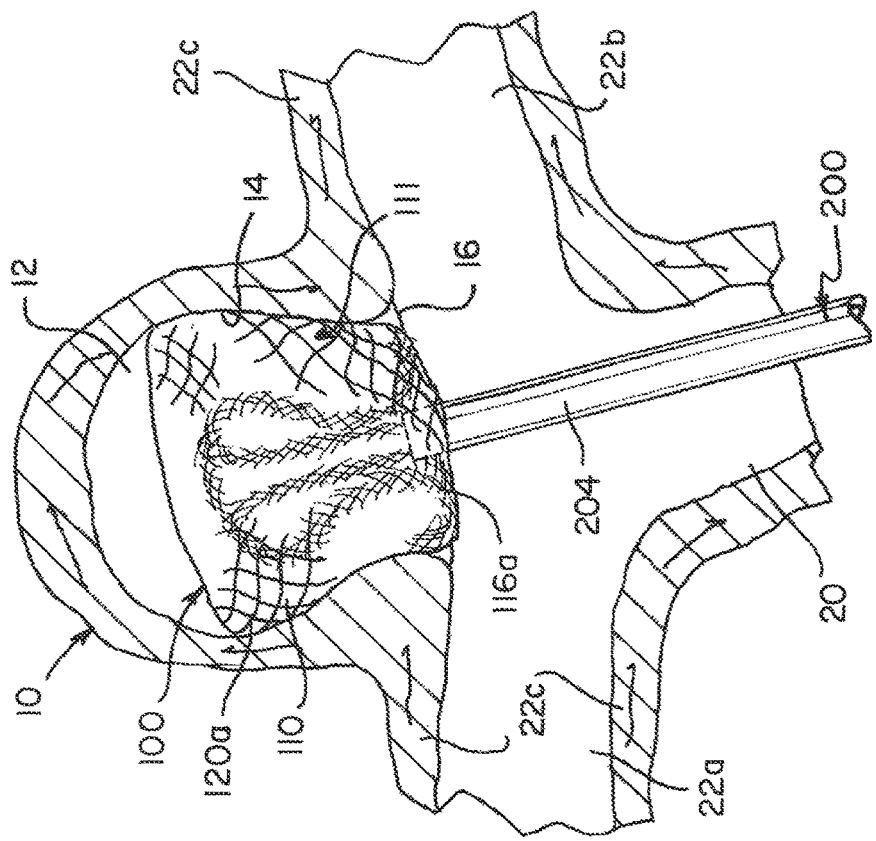
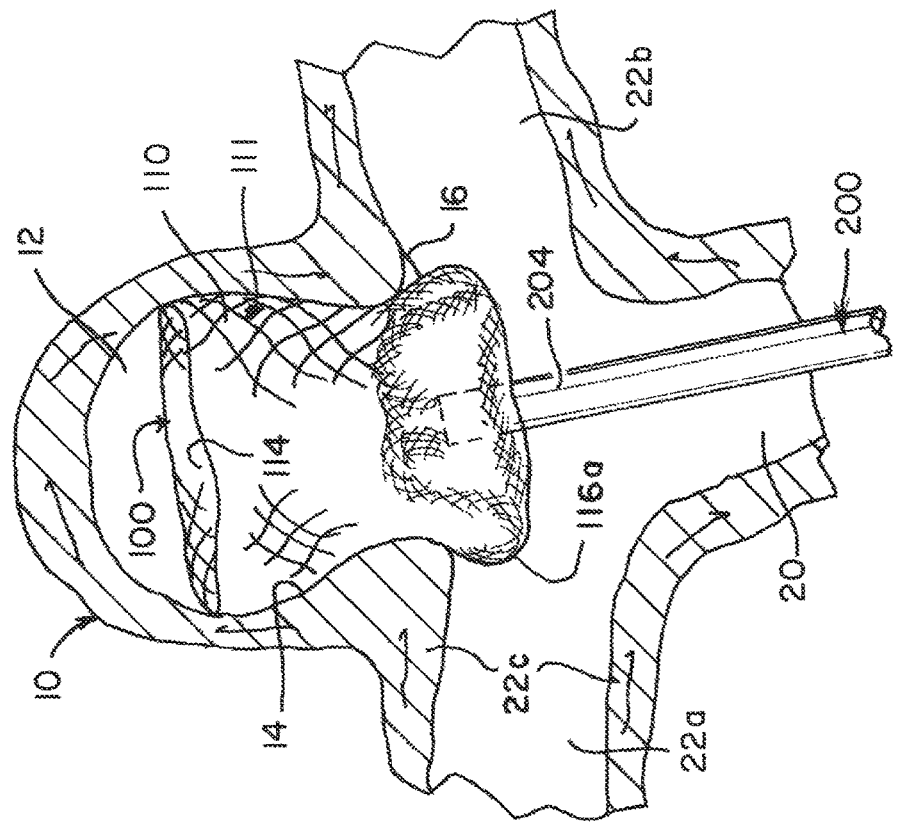
FIG. 2C
FIG. 2D

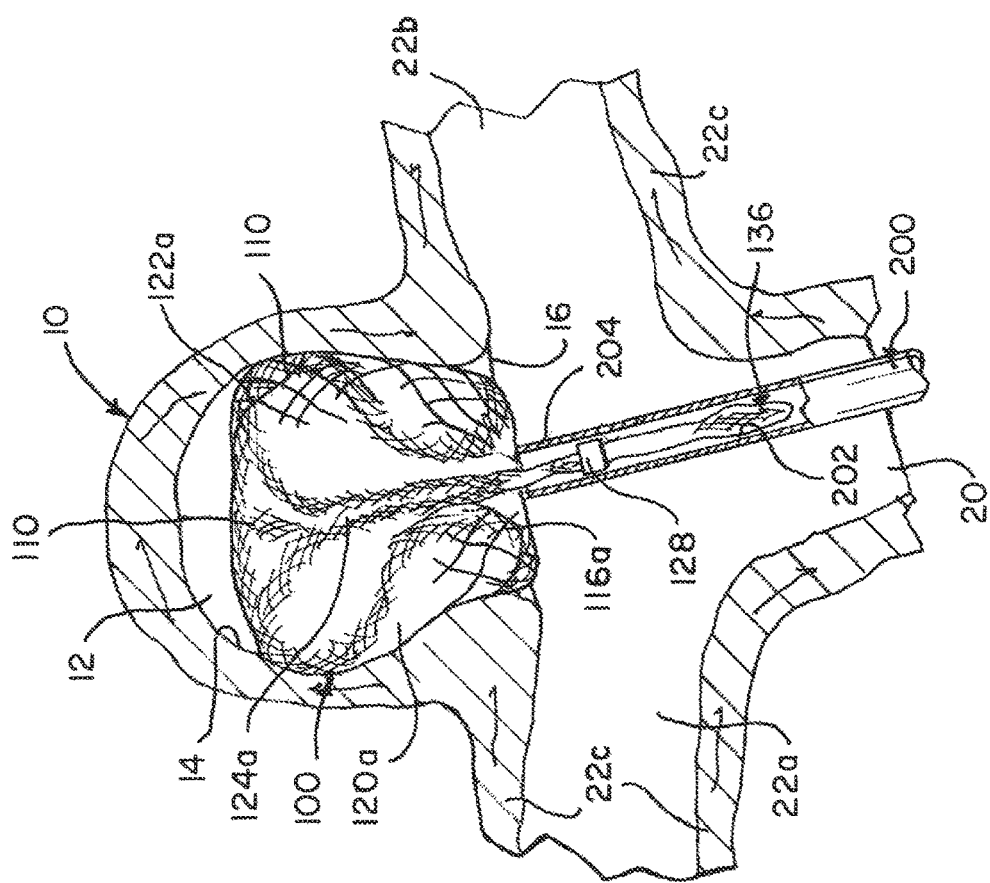

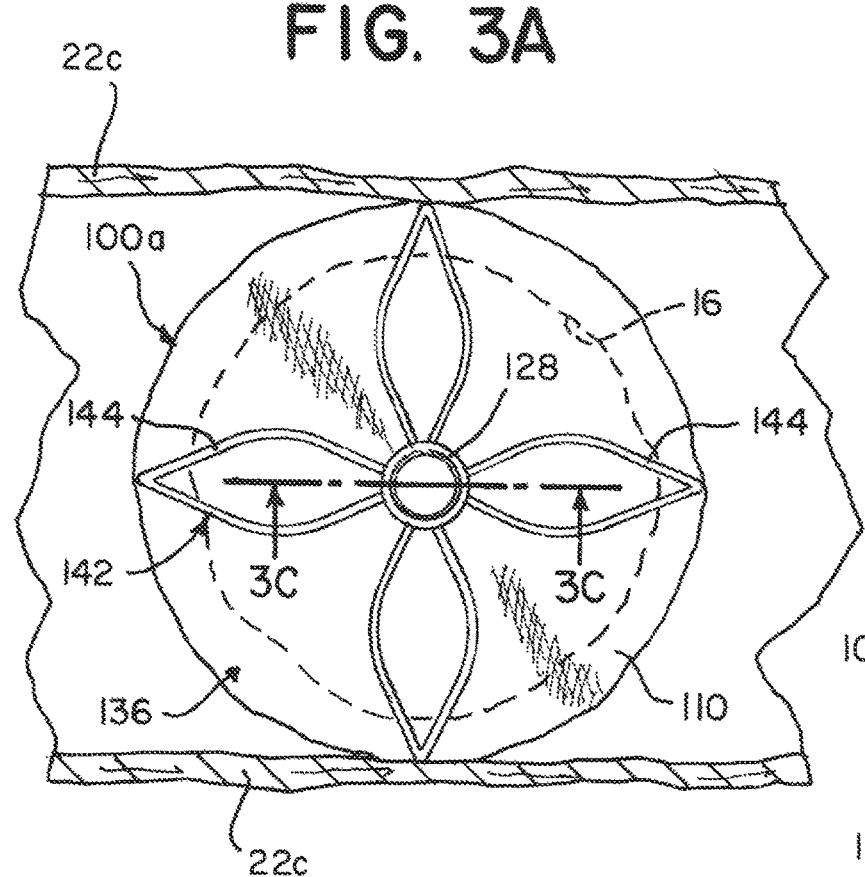
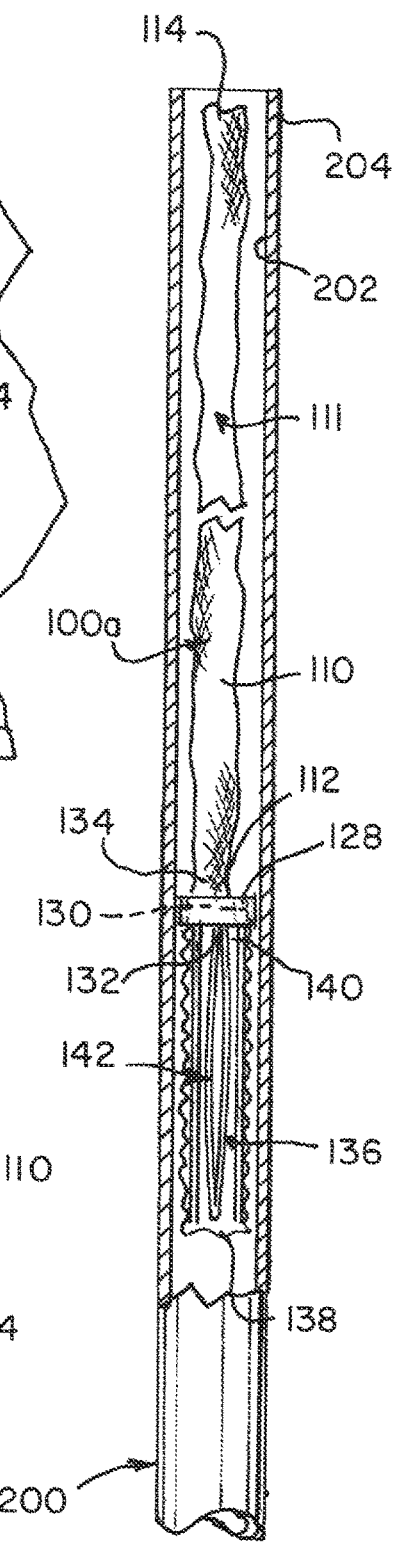
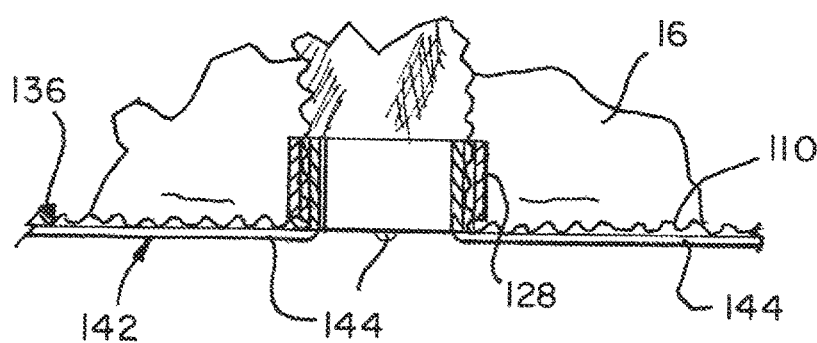

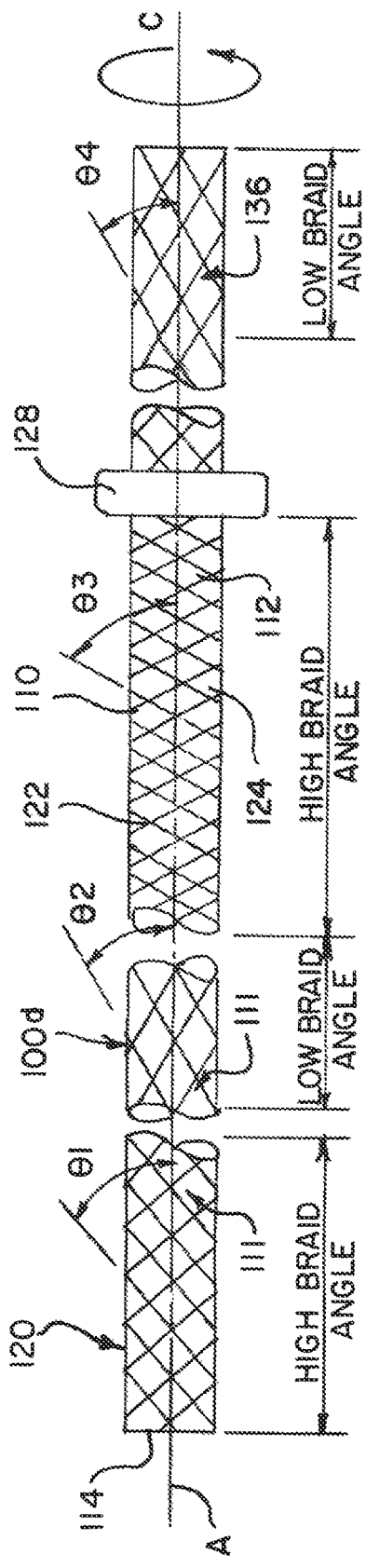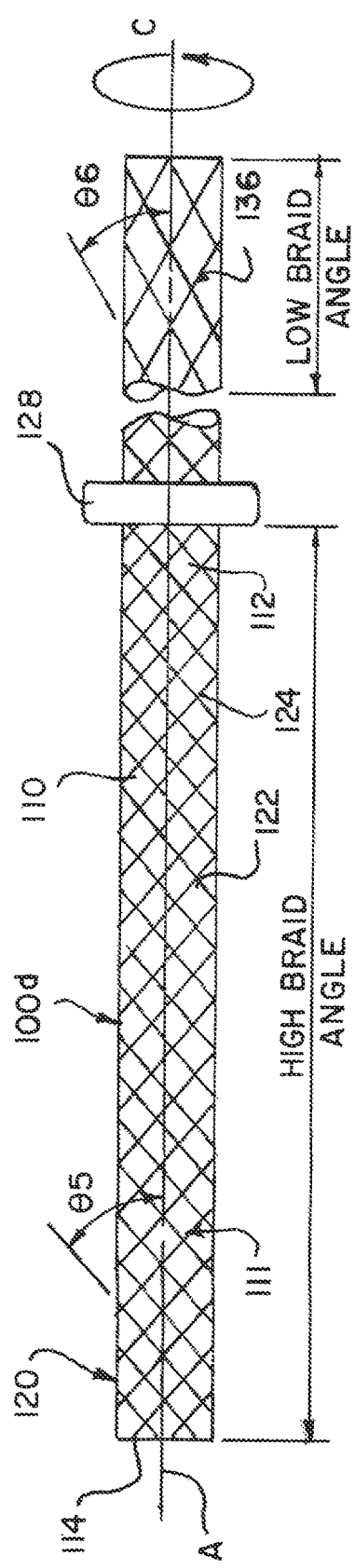

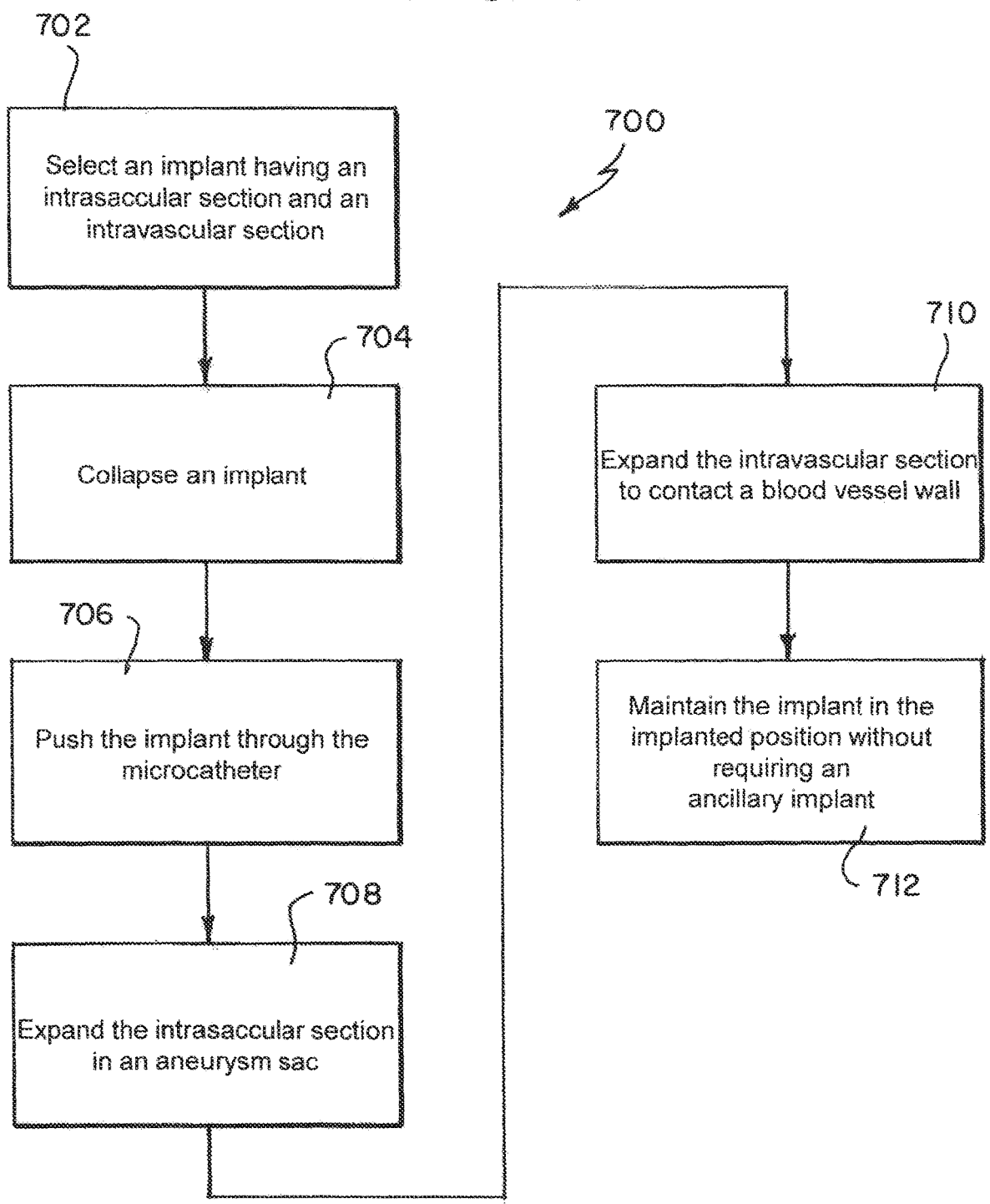

IMPLANT HAVING AN INTRASACCULAR SECTION AND INTRAVASCULAR SECTION

FIELD OF INVENTION

The present invention generally relates to medical instruments, and more particularly, to embolic implants for aneurysm therapy.

BACKGROUND

Cranial aneurysms can be complicated and difficult to treat due to their proximity to critical brain tissues. Prior solutions have included endovascular treatment whereby an internal volume of the aneurysm sac is removed or excluded from arterial blood pressure and flow. Current alternatives to endovascular or other surgical approaches can include intravascularly delivered treatment devices that fill the sac of the aneurysm with embolic material or block the entrance or neck of the aneurysm. Both approaches attempt to prevent blood flow into the aneurysm. When filling an aneurysm sac, the embolic material clots the blood, creating a thrombotic mass within the aneurysm. When treating the aneurysm neck, blood flow into the entrance of the aneurysm is inhibited, inducing venous stasis in the aneurysm and facilitating a natural formation of a thrombotic mass within the aneurysm.

Current intravascularly delivered devices typically utilize multiple embolic coils to either fill the sac or treat the entrance of the aneurysm. Naturally formed thrombotic masses formed by treating the entrance with embolic coils can result in improved healing compared to aneurysm masses packed with embolic coils because naturally formed thrombotic masses can reduce the likelihood of distention from arterial walls and facilitate reintegration into the original parent vessel shape along the neck plane. However, embolic coils delivered to the neck of the aneurysm can potentially have the adverse effect of impeding the flow of blood in the adjoining blood vessel, particularly if the entrance is overpacked. Conversely, if the entrance is insufficiently packed, blood flow can persist into the aneurysm. Treating certain aneurysm morphology (e.g. wide neck, bifurcation, etc.) can require ancillary devices such a stents or balloons to support the coil mass and obtain the desired packing density. Once implanted, the coils cannot easily be retracted or repositioned. Furthermore, embolic coils do not always effectively treat aneurysms as aneurysms treated with multiple coils often recanalize or compact because of poor coiling, lack of coverage across the aneurysm neck, blood flow, or large aneurysm size.

Alternatives to embolic coils are being explored, for example a tubular braided implant is disclosed in US Patent Publication Number 2018/0242979, which prior application is hereby incorporated herein by reference in its entirety herein into this application as if set forth in full. Tubular braided implants have the potential to easily, accurately, and safely treat an aneurysm or other arterio-venous malformation in a parent vessel without blocking flow into perforator vessels communicating with the parent vessel. Compared to embolic coils, however, tubular braided implants are a newer technology, and there is therefore capacity for improved geometries, configurations, delivery systems, etc. for the tubular braided implants.

Applicants therefore recognize a need for improved methods, devices, and systems for implants for aneurysm treatment.

SUMMARY

It is an object of the present invention to provide systems, devices, and methods to meet the above-stated needs.

An example implant can have a tubular braid. The tubular braid can have an intrasaccular section, an intravascular section, a pinched section, and a predetermined shape. In the predetermined shape, the intrasaccular section can have a sack and an opening. The pinched section can be positioned approximate the opening. The intravascular section can be substantially disk shaped and positioned to occlude the opening. The tubular braid can be movable from a collapsed shape sized to traverse a catheter to an implanted shape based at least in part on the predetermined shape. In the implanted shape, the intrasaccular section of the braid can be sized to be positioned within an aneurysm's sac and the intravascular section of the braid can be sized to appose a blood vessel wall approximate an aneurysm's neck.

In some examples, the tubular braid can have a first open end from which the intrasaccular section extends and a second open end from which the intravascular section extends. Further, in the predetermined shape, the intrasaccular section can have a first segment extending from the first open end to a first fold, a second segment encircled by the open end and extending from the first fold to a second fold, and a third segment surrounded by the second segment and extending from the second fold to the pinched section.

In some examples, when the tubular braid is in the predetermined shape, the first open end can have a diameter approximately equal to a maximum diameter of the second segment, and the second open end can have a diameter greater than the diameter of the first open end and the maximum diameter of the second segment.

In some examples, when the tubular braid is in the predetermined shape, the intravascular section extends across the first fold.

In some examples, the implant can also have a band affixed to the braid and positioned over the pinched section. The band can have a distal side from which the intrasaccular section of the braid extends and a proximal side from which the intravascular section of the braid extends.

In some examples, the implant can also have an expandable frame affixed to the band, movable from a collapsed configuration sized to traverse the catheter to a radially expanded configuration. Further, the expandable frame can have a plurality of substantially petal shaped struts.

In some examples, the combination of the intrasaccular section of the braid, the intravascular section of the braid, and the expandable frame are sufficient to maintain a position of the implant in relation to the aneurysm. Alternatively, or additionally, the combination of the intrasaccular section of the braid, and the intravascular section of the braid, are sufficient to maintain a position of the implant in relation to the aneurysm.

Another example implant can have a first braid having a first predetermined shape, a second braid having a second predetermined shape, and a band affixed to the first braid and the second braid. In the first predetermined shape, the first braid can have a sack having an opening. In the second predetermined shape, the second braid can be substantially disk shaped. When the first braid is in the first predetermined shape and the second braid is in the second predetermined shape, the band can be positioned approximate the opening and the second braid can be positioned to occlude the opening. Further, the first braid can be movable from a first collapsed shape sized to traverse a lumen of a microcatheter to a first deployed shape based at least in part on the first predetermined shape. In the first deployed shape, the first braid can be sized to be positioned within an aneurysm's sac. The second braid can be movable from a second collapsed shape sized to traverse the lumen of the microcatheter to a second deployed shape based at least in part on the second predetermined shape. In the second deployed shape, the second braid can be shaped to appose a blood vessel wall approximate an aneurysm's neck.

In some examples, the first braid can have a first open end. In the first predetermined shape, the first braid can have a first segment extending from the first open end to a first fold, a second segment encircled by the first open end and extending from the first fold to a second fold, and a third segment surrounded by the second segment and extending from the second fold to the band.

In some examples, when the first braid is in the first predetermined shape, the first open end can have a diameter approximately equal to a maximum diameter of the second segment. When the second braid is in the second predetermined shape, the second braid can have a second open end having a diameter greater than the diameter of the first open end and the diameter of the second segment. Further, the first braid can have a first braid angle and the second braid can have a second braid angle. The first braid angle can be different from the second braid angle.

In some examples, when the first braid is in the first predetermined shape and the second braid is in the second predetermined shape, the second braid can extend across the first fold.

In some examples, the example implant can have an expandable frame affixed to the band. The expandable frame can be movable from a collapsed configuration sized to traverse the lumen of the microcatheter to a radially expanded configuration.

In some examples, the expandable frame can have a plurality of substantially petal shaped struts. Further, in some examples, the combination of the first braid, the second braid, and the expandable frame can be sufficient to maintain a position of the implant in relation to an aneurysm. Alternatively, or additionally, a combination of the first braid and the second braid can be sufficient to maintain a position of the implant in relation to the aneurysm.

An example method for inserting an implant into an aneurysm having an intrasaccular braided section and an intravascular braided section can include one or more of the following steps presented in no particular order, and the method can include additional steps not included here. The method can include selecting an implant having an intrasaccular braided section and an intravascular braided section affixed to the intrasaccular braided section such that the intravascular braided section and the intrasaccular braided section are each constricted where the two sections are affixed to each other. Further, the implant can be collapsed to fit within a microcatheter. The method can include pushing the implant through a majority of the microcatheter. Further, the intrasaccular braided section can be expanded to anchor within a sac of the aneurysm. The method can further include expanding the intravascular braided section to appose a blood vessel wall approximate a neck of the aneurysm.

In some examples, the method can further include maintaining both the intrasaccular braided section within the aneurysm's sac and the intravascular braided section to appose the blood vessel wall without requiring an ancillary implant.

In some examples, the method can further include expanding the expandable frame to appose the blood vessel wall approximate the aneurysm's neck.

In some examples, the method can further include maintaining both the intrasaccular braided section within the aneurysm's sac and the intravascular braided section within a blood vessel to appose the blood vessel wall. The intravascular braided section can include the expandable frame to appose the blood vessel wall without requiring an ancillary implant. Additionally, or alternatively, the method for maintaining both the intrasaccular braided section within the aneurysm's sac and the intravascular braided section within the blood vessel to appose the blood vessel wall can be accomplished without the expandable frame.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1C is an illustration of an example implant in an implanted shape according to aspects of the present invention;

FIG. 1D is an illustration of an example implant in a deformed shape according to aspects of the present invention;

FIGS. 2A to 2F are illustrations of an implant having a tubular braid that expands to an implanted shape similar to as illustrated in FIG. 1B as the tubular braid exits a microcatheter according to aspects of the present invention;

FIG. 3A is an illustration of an example implant in an implanted shape according to aspects of the present invention;

FIG. 3B is an illustration of an example implant in a deformed shape according to aspects of the present invention;

FIG. 3C is a cross section of the example implant as indicated in FIG. 3A according to aspects of the present invention;

FIGS. 6A and 6B is an illustration of example braid angles for an example implant according to aspects of the present invention; and FIG. 7 is a flow diagram outlining example method steps that can be carried out during deployment of an exemplary implant according to aspects of the present invention.

DETAILED DESCRIPTION

Examples presented herein generally include a braided implant that can secure within an aneurysm sac and occlude a majority of the aneurysm's neck. The implant can include a tubular braid with an intravascular section and an intrasaccular section that can be set into a predetermined shape. Furthermore, the implant can be compressed for delivery through a microcatheter and implanted such that the intrasaccular section can be positioned within the sac of the aneurysm. The intravascular section can be positioned outside the sac of the aneurysm. The shapes of the intrasaccular section and the intravascular section are based on the predetermined shape and the geometry of the aneurysm in which the braid is implanted. When implanted, the intravascular section stabilizes the implant by securing it to the blood vessel walls.

Figure 1A:
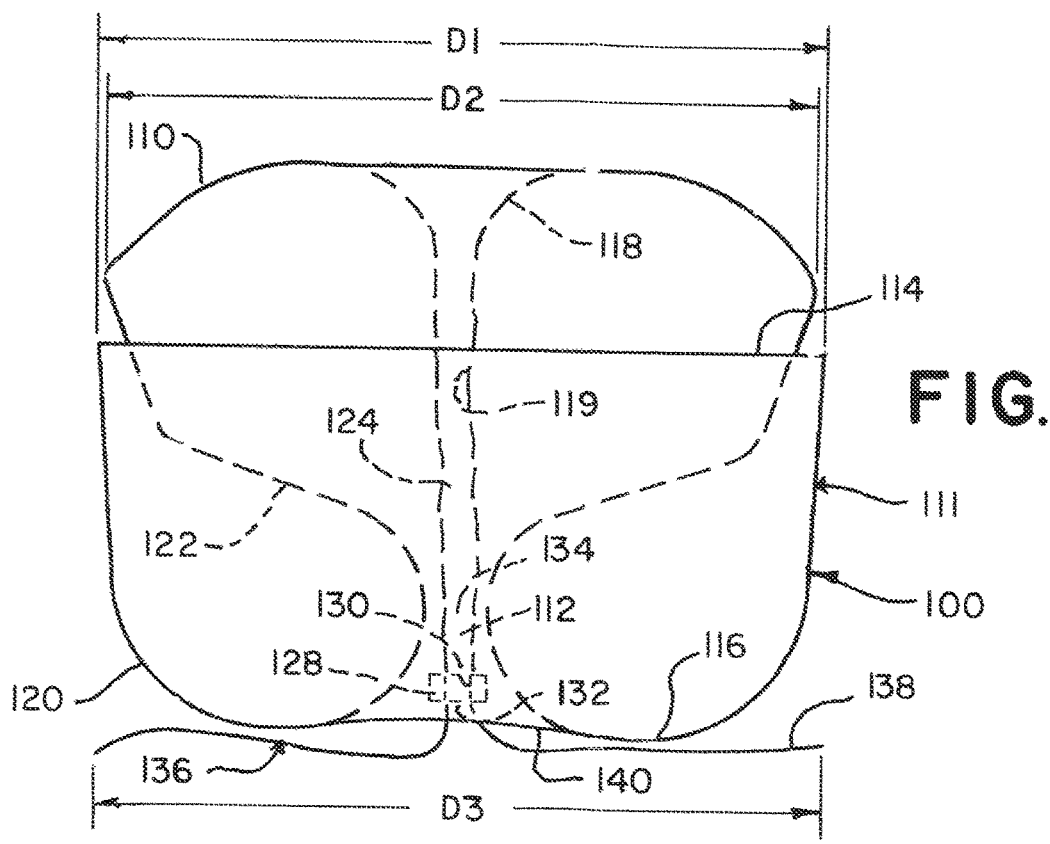
FIG. 1A is an illustration of an example implant in a predetermined shape according to aspects of the present invention.

FIG. 1A depicts a cross-sectional view of an exemplary implant in a predetermined shape. As illustrated, the implant can have a braid 110 that can include an intrasaccular section 111 and an intravascular section 136. The intrasaccular section 111 and the intravascular section 136 can be constructed from a single braid 110 or a plurality of braids. The intrasaccular section 111 can include a pinched section 112, an open end 114, a first fold 116, a second fold 118, a braid lumen 119, and a braid opening 126. Further, the intrasaccular section 111 can include a first segment 120 extending from the open end 114 to the first fold 116, a second segment 122 extending from the first fold 116 to the second fold 118, and a third segment 124 extending from the second fold 118 to the pinched section 112. The third segment 124 can be surrounded by the second segment 122. Alternatively, the third segment 124 can extend from the second fold 118 to the proximal end 138 of the intravascular section 136. Further, the intrasaccular section 111 can include a band 128, a band lumen 130, a distal side 134 of the band 128, and a proximal side 132 of the band 128. The band 128 can be disposed proximate the pinched section 112 of the braid 110. In some examples, the band 128 can be a weld or an adhesive. The braid 110 can be attached to the band lumen 130. Where the intrasaccular section 111 and the intravascular section 136 are constructed from the same braid 110, the braid 110 can pass through the band lumen 130 to form the intravascular section 136. Alternatively, where the intrasaccular section 111 and the intravascular section 136 are constructed from independent braids, the braid lumen 119 can be attached to the distal side 134 of the band 128, and the distal end 140 of the intravascular section 136 can be attached to the proximal side 132 of the band 128. The first segment 120 can have a diameter D1, the second segment 122 can have a diameter D2, and the intravascular section 136 can have a diameter D3. The diameter D3 can be a measure from the distal end 140 of the intravascular section 136 to a proximal end 138 of the intravascular section 136, the measure then multiplied by two. The diameter D3 of the intravascular section 136 can be greater than the diameter D1 of the first segment 120. The diameter D2 of the second segment 122 can be less than the diameter D1 of the first segment 120. In other words, D3>D1>D2. Alternatively, the diameter D2 can be approximately equal to the diameter D1.

Figure 1B:
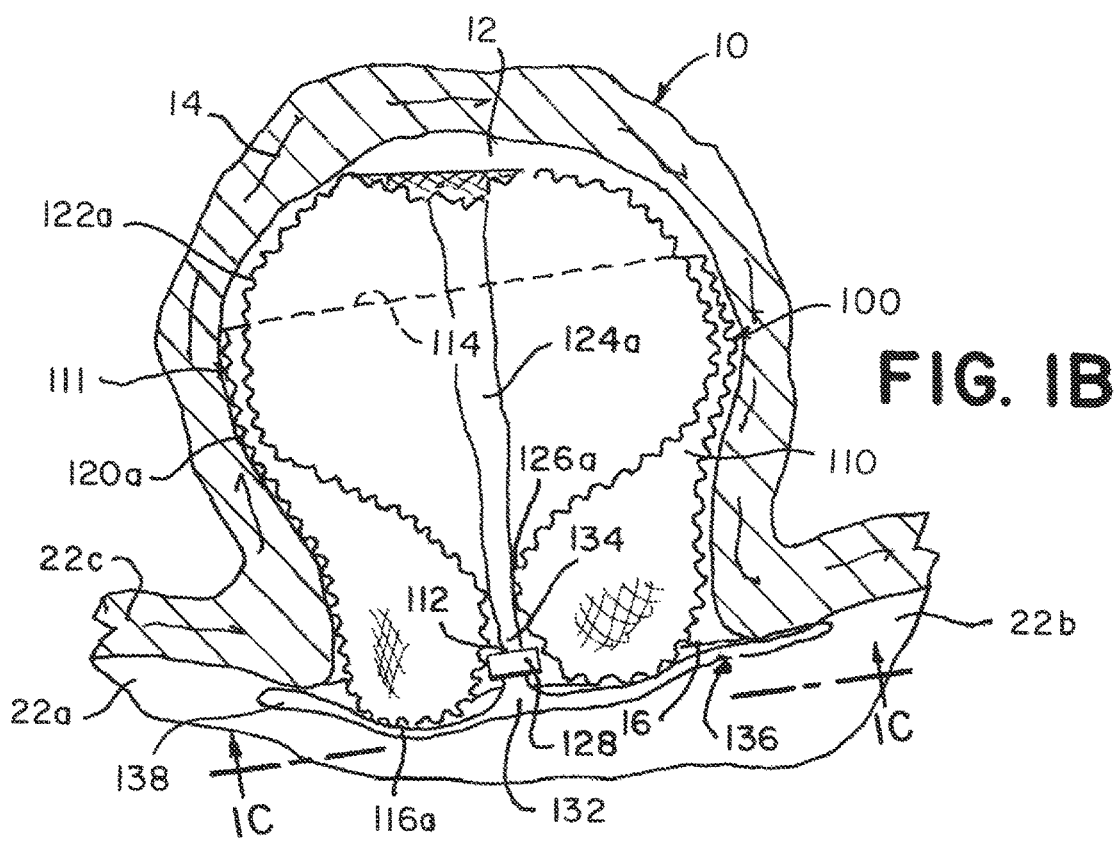
FIG. 1B is an illustration of an example implant in an implanted shape according to aspects of the present invention.

FIG. 1B depicts a cross-sectional view of an exemplary implant in an implanted shape as indicated in FIG. 1C. As illustrated, the implant 100 can include an intrasaccular section 111 and an intravascular section 136. The intrasaccular section 111 can be positioned within a sac 12 of an aneurysm 10 and the intravascular section 136 can be positioned in vasculature 22a, 22b such that it occludes the neck 16 of the aneurysm 10. The proximal end 138 of the intravascular section 136 can appose or anchor to the blood vessel wall 22c. Since the implant 100 is constrained by the aneurysm wall 14 and blood vessel wall 22c, the implanted shape, as illustrated, can be distorted from the predetermined shape, as discussed in FIG. 1A above. The intrasaccular section 111 can include an open end 114, a pinched section 112, a proximal fold 116a, a distal fold 118a, and a braid opening 126a. A band 128 can be disposed proximate the pinched section 112. The band 128 can have a distal side 134, a proximal side 132, and a band lumen 130. In some examples, the band 128 can be a weld or an adhesive. An outer layer 120a extends from the open end 114 to the proximal fold 116a. A middle layer 122a extends from the proximal fold 116a to the distal fold 118a, and an inner layer 124a extends from the distal fold 118a to the pinched section 112. Alternatively, or additionally, when the intrasaccular section 111 and the intravascular section 136 are constructed from a single braid 110, the inner layer can extend from the distal fold 118a to the proximal end 138 of the intravascular section 136. Alternatively, or additionally, when the intrasaccular section 111 and the intravascular section 136 are constructed from a plurality of braids, the inner layer 124a can extend from the distal fold 118a to the pinched section 112. Further, when independent braids are utilized, the inner layer 124a can be attached to the distal side 134 of the band 128 and another braid can begin at a distal end 140 of the intravascular section 136 can be attached to the proximal side 132 of the band 128.

FIG. 1C depicts a cross-sectional view of the implant 100 in the implanted shape as indicated in FIG. 1B. As illustrated, the intravascular section 136 secures itself by apposing or anchoring to the blood vessel wall 22c. Note that the intravascular section 136 extends beyond the aneurysm neck 16 and in doing so, provides greater stability to the intrasaccular section 111 positioned within the sac 12 of the aneurysm 10. The intravascular section 136 can be sufficient to anchor the implant 100 in place.

FIG. 1D depicts an exemplary implant in a deformed shape. As illustrated, the implant 100 can include an intrasaccular section 111 and an intravascular section 136. The implant 100 can be positioned in a deformed shape within a lumen 202 of a microcatheter 200. The implant can be positioned such that the open end 114 of the implant 100 can be proximate a distal end 204 of the microcatheter 200.

Figure 2A:
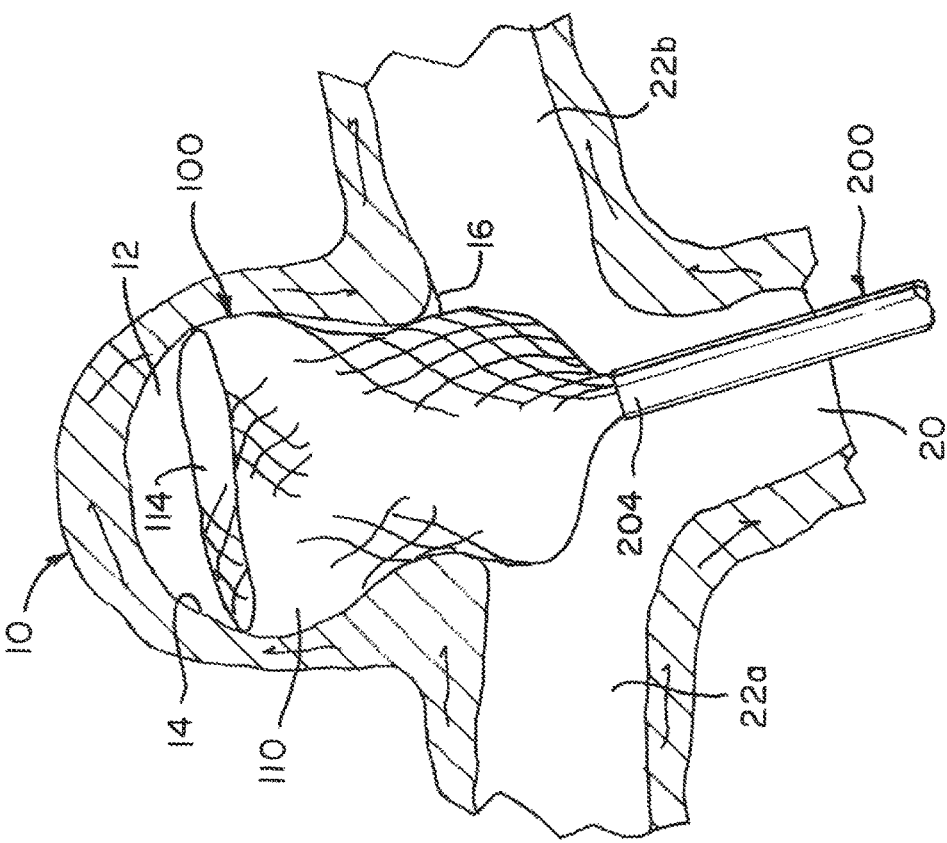
Figure 2B:
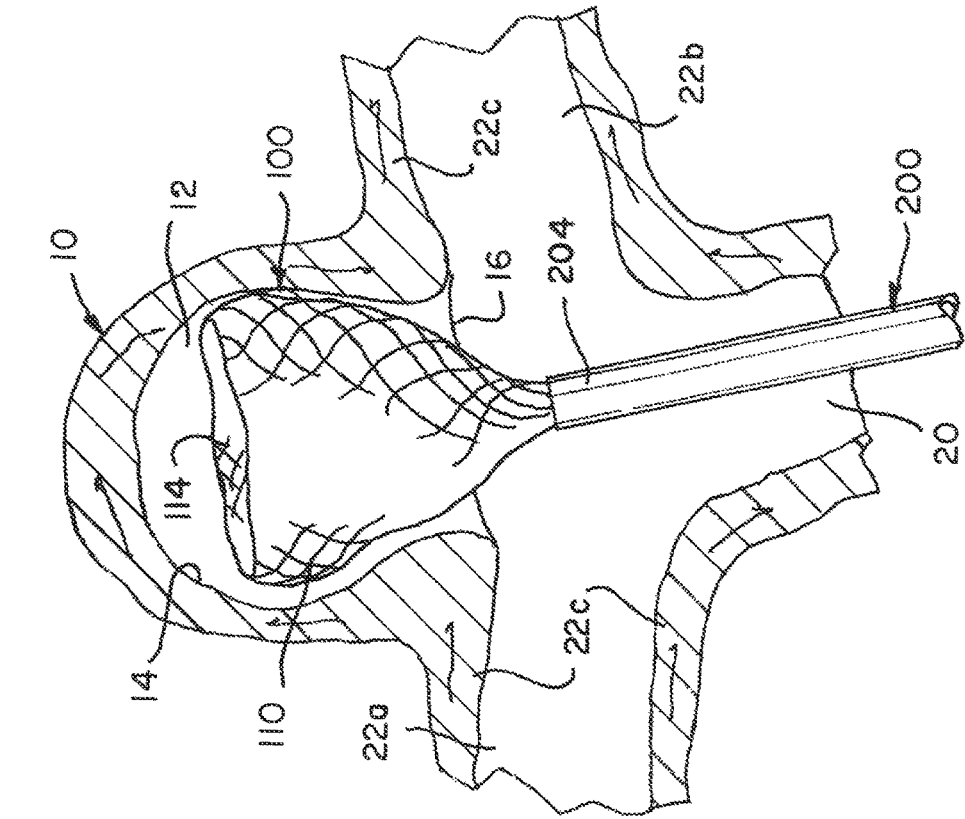

FIGS. 2A to 2F depict an exemplary implant being deployed. As illustrated, in FIG. 2A, the distal end 204 of the microcatheter 200 can be inserted through the stem vessel 20 and the implant 100 can be deployed by pushing the implant 100 out of the distal end 204 of the microcatheter 200 and into the sac 12 of the aneurysm 10. Alternatively, or additionally, the aneurysm 10 can be located on a blood vessel wall 22c without the stem vessel 20 (e.g. a sidewall aneurysm). In FIG. 2B, the distal end 204 of the microcatheter 200 can be slightly retracted in a proximal direction and more of the implant 100 can be pushed out of the distal end 204 of the microcatheter 200. Note, that the braid 110 begins to contact the aneurysm wall 14. In FIG. 2C, the proximal fold 116a and the outer layer 120a begin to develop as the braid 110 continues to invert. The band 128 and the intravascular section 136 still remain within the lumen 202 of the microcatheter 200. In some examples, the band 128 can be a weld or an adhesive. In FIG. 2D, the braid 110 continues to invert as the proximal fold 116a and the outer layer 120a become more defined. In FIG. 2E, as the braid 110 continues to invert, the middle layer 122a begins to develop along with the distal fold 118a and the inner layer 124a. In FIG. 2F, the band 128 and the intravascular section 136 are no longer within the lumen 202 of the microcatheter 200. In some examples, the band 128 can be a weld or an adhesive. The intravascular section 136 having a proximal end 138 blooms to occlude the neck 16 and provide greater stability to the intrasaccular section 111 of the implant 100 positioned within the sac 12. The proximal end 138 of the intravascular section 136 stabilizes and secures the implant 100 by applying pressure to the blood vessel wall 22c. The microcatheter 200 can be retracted from the stem vessel 20.

FIG. 3A depicts a cross-sectional view of an exemplary implant utilizing an expandable frame 142. As illustrated, implant 100a can include an intravascular section 136. The intravascular section 136 can include an expandable frame 142. The expandable frame 142 can provide additional stability to the implant 100a by providing a reinforcing structure to the intravascular section 136. The expandable frame 142 can include one or more petals 144 constructed from nitinol. Alternatively, or additionally, the expandable frame 142 can be constructed from platinum wire.

FIG. 3B depicts the implant 100a in a deformed shape, the implant 100a can include an intravascular section 136 having an expandable frame 142. The implant 100a is illustrated in a collapsed, delivery configuration within the lumen 202 of the microcatheter 200 such that the open end 114 of the implant 100a can be proximate the distal end 204 of the microcatheter 200.

FIG. 3C depicts a cross-sectional view of the implant 100a as indicated in FIG. 3A.

Figure 4A:
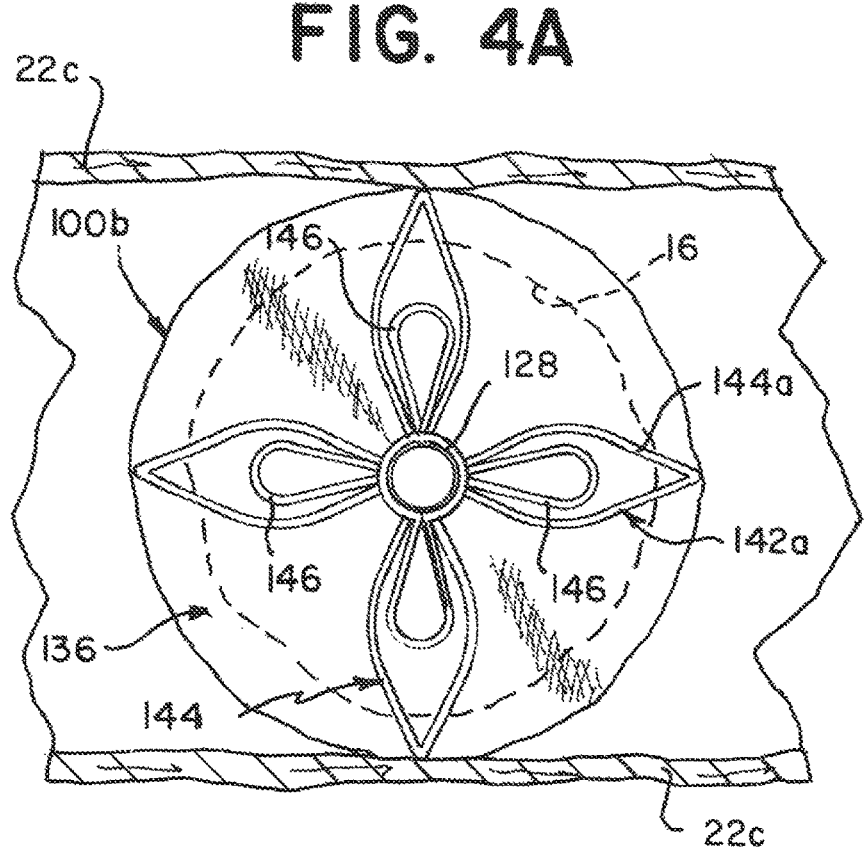
FIG. 4A is an illustration of an example implant in an implanted shape according to aspects of the present invention.

FIG. 4A depicts a cross-sectional view of another exemplary implant 100b utilizing an expandable frame. As illustrated, implant 100b can include an intravascular section 136. The intravascular section 136 can include an expandable frame 142a. The expandable frame 142a can provide additional stability to the implant 100b by providing a reinforcing structure to the intravascular section 136. The expandable frame 142a can include one or more petals 144a constructed from nitinol. Alternatively, or additionally, the expandable frame 142a can be constructed from platinum wire. Further, one or more inner petals 146 can be positioned within the one or more petals 144a.

Figure 4B:
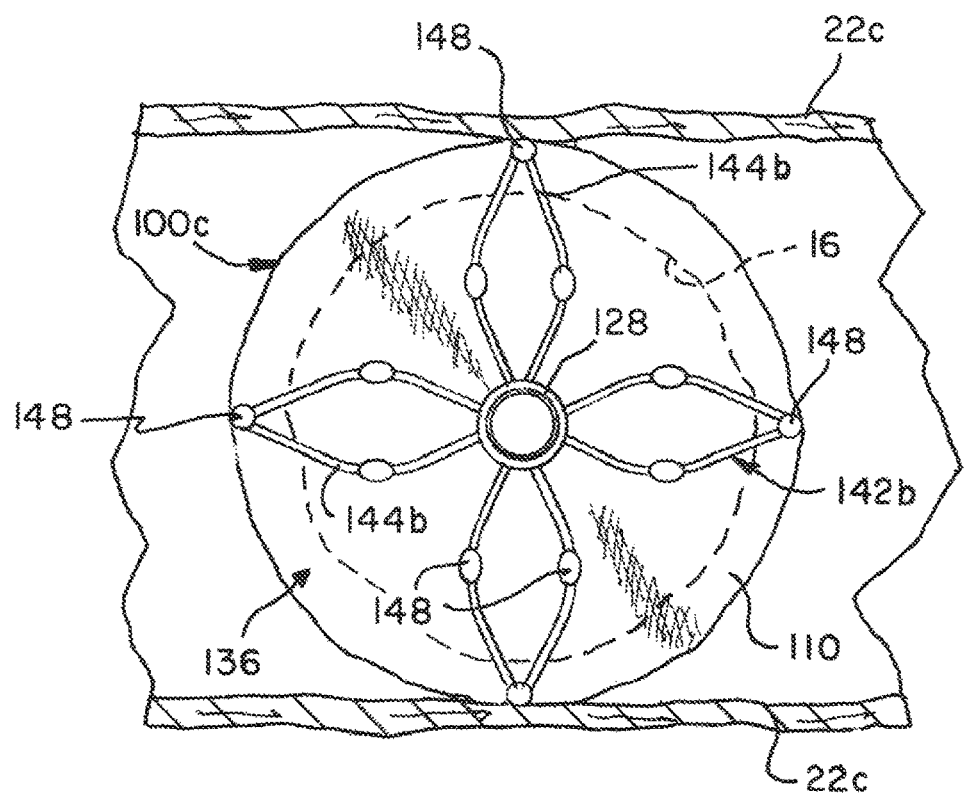
FIG. 4B is an illustration of an example implant in an implanted shape according to aspects of the present invention.

FIG. 4B depicts a cross-sectional view of another exemplary implant 100c utilizing an expandable frame 142b. As illustrated, implant 100c can include an intravascular section 136. The intravascular section 136 can include an expandable frame 142b. The expandable frame 142b can provide additional stability to the implant 100c by providing a reinforcing structure to the intravascular section 136. The expandable frame 142b can include one or more petals 144b constructed from nitinol. Additionally, or alternatively, the expandable frame 142b can include one or more petals 144b constructed from platinum wire. The one or more petals 144b can further include radiopaque markers 148 disposed on the one or more petals 144b.

Figure 5A:
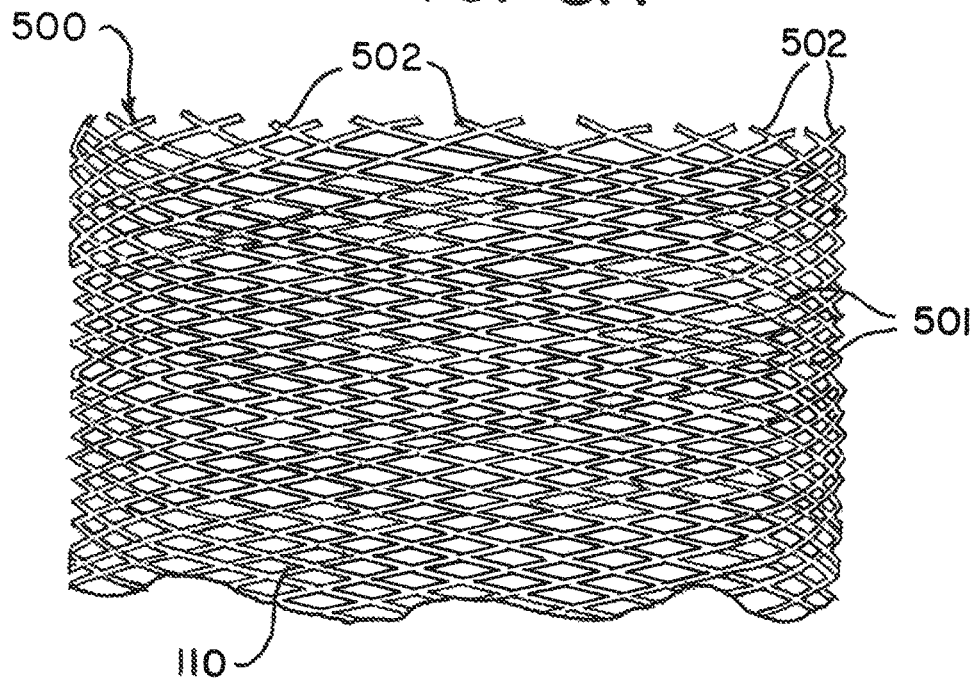
FIGS. 5A and 5B are illustrations of example braid types for an example implant according to aspects of the present invention.
Figure 5B:
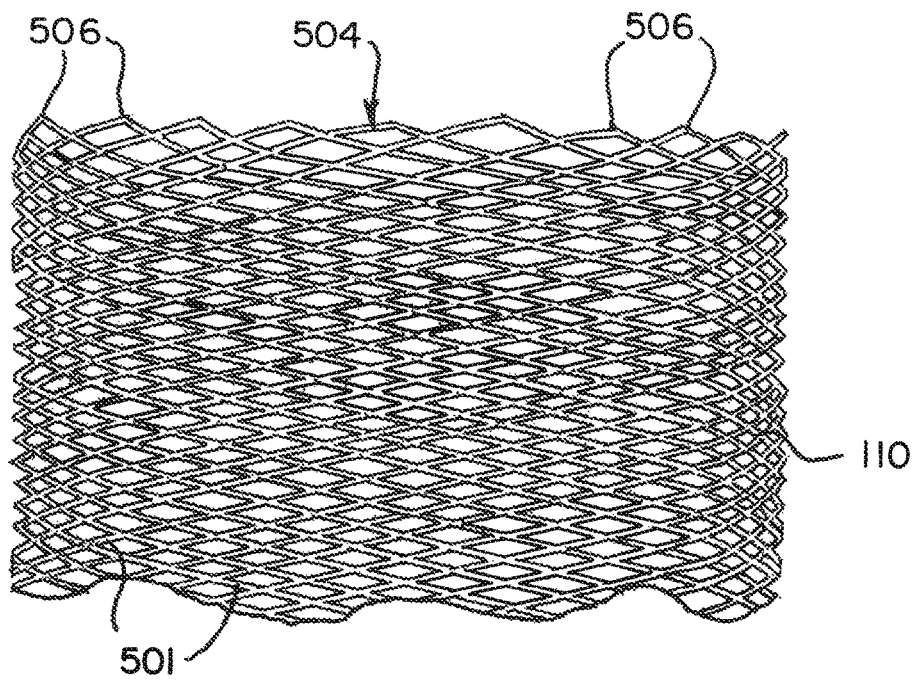

FIGS. 5A and 5B depict examples of different weaves that can be employed in constructing the braid 110. FIG. 5A, for example, illustrates a barbed weave that can have strands 501 and sharp tips 502 by virtue of the ends of the braid 110 being cut. These sharp tips 502 can pierce or prick at the blood vessel wall 22c or the aneurysm wall 14 and can potentially destabilize the aneurysm 10 leading to a rupture. In contrast, FIG. 5B illustrates an atraumatic weave that can include blunt tips 506 that can reduce the ability for the braid 110 to pierce the aneurysm wall 16 or the blood vessel wall 22c. The blunt tips 506 can be formed by bending or folding the strands 501 at the end of the braid 110, instead of simply cutting the strands 501 as discussed above in FIG. 5A.

FIGS. 6A and 6B depict an exemplary implant 100d having a braid 110 configured to have one or more braid angles, for example, braid angles $\theta1$, $\theta2$, $\theta3$, and $\theta4$ which can be measured by comparing the tangential trajectory of a braid strand to the central axis A, as illustrated, and as would otherwise be understood by a person of ordinary skill in the art according to the teachings herein. A contiguous braided portion can include sections having different braid angles. For instance, a braid can be wrapped around a mandrel. While the wires are woven around the mandrel, the mandrel can move at a variable speed, with a faster moving mandrel resulting in a lower braid angle and the mandrel moving at a slower speed resulting in a higher braid angle. A braid having a variable braid angle can otherwise be formed as appreciated and understood by a person of ordinary skill in the art. Braid strands can be woven such that about half of the strands wrap in a clockwise helix, the other half wraps in a counterclockwise helix, and the oppositely wrapping strands cross over and under each other in an alternating fashion. Constructed as such, portions of the braid having a higher braid angle can therefore having a higher density of strands compared to portions of the braid having lower braid angle. Higher strand density can result in a denser, stiffer braid portion.

The braid 110 can include a number of strands, each extending from the open end 114 to the proximal end 140 of the intravascular section 136 and helically wrapping about the circumference C. Alternatively, or additionally, the braid 110 can include a first set of strands, each extending from the open end 114 to the band 128, and a second set of strands extending from the band 128 to the proximal end 140 of the intravascular section 136 and helically wrapping about the circumference C. In some examples, the band 128 can be a weld or an adhesive. As illustrated in FIG. 6A, the first set of strands can have one or more first braid angles $\theta1$, $\theta2$, $\theta3$, and the second set of strands can one or more second braid angles $\theta4$. The braid angle $\theta4$ of the intravascular section 136 can be less than braid angles $\theta1$ or $\theta3$ of the intrasaccular section 111 to reduce foreshortening of the intravascular section 136 when the intravascular section 136 exits the distal end 204 of the microcatheter 200. Further, braid angle $\theta2$ can also have a braid angle less than braid angles $\theta1$ or $\theta3$. The reduction in foreshortening is advantageous because it can make the implant 100d easier to control. As discussed above, segments having a higher braid angle $\theta1$, $\theta3$ can be stiffer than segments having a lower braid angle $\theta2$, $\theta4$ resulting in a better anchor for the implant 100d. Alternatively, or additionally, as illustrated in FIG. 6B, the intrasaccular section 111, can have at least one braid angle $\theta5$. Braid angle $\theta5$ can be associated with the first segment 120, the second segment 122, and the third segment 124. Alternatively, or additionally, as illustrated in FIG. 6B, the intravascular section 136 can have a braid angle $\theta6$. In some example, braid angles $\theta5$ can have a higher braid angle than braid angle $\theta6$. This can allow the intravascular section 136 to be easier to control during placement. A properly positioned intravascular section 136 can function as a better anchor for the implant 100d compared to a foreshortened section 136. Further, since the first segment 120 can also be stiffer than second segment 122 and the third segment 124, the first segment 120 can also behave as an anchor for the implant 100d. It is envisioned that the features described in relation to FIGS. 6A and 6B can be combinable with other exemplary implants 100, 100a, 100b, 100c as illustrated and described throughout herein.

FIG. 7 illustrates an example method 700 for deploying an exemplary implant into an aneurysm as presented herein, variations thereof, or alternatives thereof as would be appreciated and understood by a person of ordinary skill in the art.

At block 702, the method 700 can include selecting an implant 100b having an intrasaccular section 111 and an intravascular section 136 affixed to the intrasaccular section 111 such that the intravascular section 136 and the intrasaccular section 111 are each constricted where the two sections are affixed to each other. At block 704, the implant 100b can be collapsed to fit within a lumen 202 of a microcatheter 200. At block 706, the method 700 can include pushing the implant 100b through the lumen 202 of the microcatheter 200. At block 708, the intrasaccular section 111 can be expanded to anchor within a sac 12 of the aneurysm 10.

At block 710, the method 700 can further include expanding the intravascular section 136 to appose a blood vessel wall 22c approximate a neck 14 of the aneurysm 10. The method 700 can further include expanding the expandable frame 142a to appose the blood vessel wall 22c approximate the aneurysm's neck 14. At block 712, the method 700 can further include maintaining the intrasaccular section 111 within the aneurysm's sac 12 and the intravascular section 136 to appose the blood vessel wall 22c without requiring an ancillary implant. The method 700 can additionally, or alternatively, include maintaining the intrasaccular section 111 within the aneurysm's sac 12, the intravascular section 136 to appose the blood vessel wall 22c, and the expandable frame 142a to appose the blood vessel wall 22c without requiring an ancillary implant.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

When used herein, the terms "tubular" and "tube" are to be construed broadly and are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered or curved outer surface without departing from the scope of the present invention.

The descriptions contained herein are examples of embodiments of the invention and are not intended in any way to limit the scope of the invention. As described herein, the invention contemplates many variations and modifications of the implant system, including alternative geometries of elements and components described herein, alternative braid shapes, utilizing one or more of several means for braiding, knitting, weaving, or otherwise forming the braid, utilizing alternative materials for each component or element (e.g. radiopaque materials, memory shape materials, polymers, metals, etc.), utilizing additional components to perform functions described herein or not described herein as would be apparent to those having ordinary skill in the art to which this invention relates. Such variations and modifications are intended to be within the scope of the claims which follow.

What is claimed is:
1. An implant comprising:
   a tubular braid comprising an intrasaccular section, an intravascular section, a pinched section, and a predetermined shape,
   wherein, in the predetermined shape, the intrasaccular section comprises a sack comprising an opening, the pinched section is positioned approximate the opening, and the intravascular section is substantially disk shaped and positioned to occlude the opening,
   wherein the tubular braid is movable from a collapsed shape sized to traverse a catheter to an implanted shape based at least in part on the predetermined shape, and
   wherein, in the implanted shape, the intrasaccular section of the braid is sized to be positioned within an aneurysm's sac and the intravascular section of the braid is sized to appose a blood vessel wall approximate an aneurysm's neck,
   wherein the tubular braid comprises a first open end from which the intrasaccular section extends and a second open end from which the intravascular section extends,
   wherein, in the first predetermined shape, the intrasaccular section comprises a first segment extending from the first open end to a first fold, a second segment encircled by the first open end and extending from the first fold to a second fold, and a third segment surrounded by the second segment and extending from the second fold to the pinched section, and
   wherein the first fold is approximate the aneurysm's neck and the second fold is approximate a distal portion of the aneurysm's sac.

2. The implant of claim 1, wherein, when the tubular braid is in the predetermined shape, the first open end comprises a diameter, approximately equal to a maximum diameter of the second segment, and the second open end comprises a diameter greater than the diameter of the first open end and the maximum diameter of the second segment.

3. The implant of claim 1, wherein, when the tubular braid is in the predetermined shape, the intravascular section extends across the first fold.

4. The implant of claim 1, further comprising:
   a band affixed to the braid and positioned over the pinched section, the band comprising a distal side from which the intrasaccular section of the braid extends and a proximal side from which the intravascular section of the braid extends.

5. The implant of claim 4, further comprising:
   an expandable frame affixed to the band, movable from a collapsed configuration sized to traverse the catheter to a radially expanded configuration.

6. The implant of claim 5, wherein the expandable frame comprises a plurality of substantially petal shaped struts.

7. The implant of claim 5, wherein the combination of the intrasaccular section of the braid, the intravascular section of the braid, and the expandable frame are sufficient to maintain a position of the implant in relation to the aneurysm.

8. The implant of claim 1, wherein the combination of the intrasaccular section and the intravascular section of the braid are sufficient to maintain a position of the implant in relation to the aneurysm.

9. An implant comprising:
   a first braid comprising a first predetermined shape;
   a second braid comprising a second predetermined shape; and
   a band affixed to the first braid and the second braid,
   wherein, in the first predetermined shape, the first braid comprises a sack comprising an opening,
   wherein, in the second predetermined shape, the second braid is substantially disk shaped,
   wherein, when the first braid is in the first predetermined shape and the second braid is in the second predetermined shape, the band is positioned approximate the opening and the second braid is positioned to occlude the opening, wherein the first braid, is movable from a first collapsed shape sized to traverse a lumen of a microcatheter to a first deployed shape based at least in part on the first predetermined shape, wherein, in the first deployed shape, the first braid is sized to be positioned within an aneurysm's sac, wherein the second braid is movable from a second collapsed shape sized to traverse the lumen of the microcatheter to a second deployed shape based at least in part on the second predetermined shape, and wherein, in the second deployed shape, the second braid is shaped to appose a blood vessel wall approximate an aneurysm's neck, wherein the first braid comprises a first open end, wherein, in the first predetermined shape, the first braid comprises a first segment extending from the first open end to a first fold, a second segment encircled by the first open end and extending from the first fold to a second fold, and a third segment surrounded by the second segment and extending from the second fold to the band, and wherein the first fold is approximate the aneurysm's neck and the second fold is approximate a distal portion of the aneurysm's sac.

10. The implant of claim 9, wherein, when the first braid is in the first predetermined shape, the first open end comprises a diameter, approximately equal to a maximum diameter of the second segment, wherein, when the second braid is in the second predetermined shape, the second braid comprises a second open end comprising a diameter greater than the diameter of the first open end and the maximum diameter of the second segment, wherein the first braid comprises a first braid angle, wherein the second braid comprises a second braid angle, and wherein the first braid angle different from the second braid angle.

11. The implant of claim 9, wherein, when the first braid is in the first predetermined shape and the second braid is in the second predetermined shape, the second braid extends across the first fold.

12. The implant of claim 9, further comprising:
an expandable frame affixed to the band, movable from a collapsed configuration sized to traverse the lumen of the microcatheter to a radially expanded configuration.

13. The implant of claim 12, wherein the expandable frame comprises a plurality of substantially petal shaped struts.

14. The implant of claim 12, wherein the combination of the first braid, the second braid, and the expandable frame are sufficient to maintain a position of the implant in relation to an aneurysm.

15. A method comprising:
selecting the implant of claim 1;
collapsing the implant to fit within a microcatheter;
pushing the implant through a majority of the microcatheter;
expanding the intrasaccular braided section to anchor within the aneurysm's sac; and
expanding the intravascular braided section to appose the blood vessel wall approximate the aneurysm's neck.

16. The method of claim 15, further comprising:
maintaining the intrasaccular braided section within the aneurysm's sac and the intravascular braided section to appose the blood vessel wall without requiring an ancillary implant.

17. The method of claim 15, wherein selecting the implant further comprises selecting the implant comprising an expandable frame, the method further comprising:
expanding the expandable frame to appose the blood vessel wall approximate the aneurysm's neck.

18. The method of claim 17, further comprising:
maintaining the intrasaccular braided section within the aneurysm's sac, the intravascular braided section to appose the blood vessel wall, and the expandable frame to appose the blood vessel wall without requiring an ancillary implant.

* * * * *